United States Patent [19]

Engel

[11] 4,335,252
[45] * Jun. 15, 1982

[54] INSECTICIDAL PYRETHROID ENANTIOMER PAIR

[75] Inventor: John F. Engel, Medina, N.Y.

[73] Assignee: FMC Corporation, Philadelphia, Pa.

[*] Notice: The portion of the term of this patent subsequent to Apr. 21, 1998, has been disclaimed.

[21] Appl. No.: 221,581

[22] Filed: Dec. 31, 1980

Related U.S. Application Data

[63] Continuation-in-part of Ser. No. 42,372, May 24, 1979, Pat. No. 4,263,319, which is a continuation of Ser. No. 927,198, Jul. 24, 1978, abandoned, and Ser. No. 870,973, Jan. 20, 1978, abandoned.

[51] Int. Cl.$^3$ .................. A01N 53/00; C07C 69/743
[52] U.S. Cl. ................................ 560/124; 424/285
[58] Field of Search ................... 560/124; 424/285

[56] References Cited

U.S. PATENT DOCUMENTS 3,647,857  3/1972  Morgan ........................... 560/124
4,183,948  1/1980  Huff ................................. 424/304
4,263,619  4/1981  Engel ............................... 424/305

OTHER PUBLICATIONS

Nakada et al., *Agric. Biol. Chem.*, 42, 1357 (1978).
Derwent Abstract No. 75226S for Japanese Pat. No. 7,140,617, patent published 12/1/71.
Derwent Abstract No. 75227S for Japanese Pat. No. 7,140,618, patent published 12/1/71.
Derwent Abstract No. 14873S for Japanese Pat. No. 7,106,918, patent published 2/20/71.

*Primary Examiner*—Richard Raymond
*Attorney, Agent, or Firm*—Robert M. Kennedy; Robert L. Andersen; H. Robinson Ertelt

[57] ABSTRACT

An insecticidal enantiomer pair consisting essentially of a substantially equimolar mixture of S-4-phenyl-2-indanyl 1R, cis-3-(2-chloro-3,3,3-trifluoro-1-propenyl)-2,2-dimethylcyclopropanecarboxylate and R-4-phenyl-2-indanyl 1S,cis-3-(2-chloro-3,3,3-trifluoro-1-propenyl)-2,2-dimethylcyclopropanecarboxylate, its preparation by liquid chromatography, and its utility as an insecticide are described and exemplified.

1 Claim, No Drawings

INSECTICIDAL PYRETHROID ENANTIOMER PAIR

The present application is a continuation-in-part of U.S. Ser. No. 042,372, filed May 24, 1979, now U.S. Pat. No. 4,263,319, which itself is a continuation, application of U.S. Ser. Nos. 927,198, filed July 24, 1978, now abandoned, and 870,973, filed Jan. 20, 1978, now abandoned, the disclosures of all of which are incorporated herein by reference.

The invention is directed to a novel alcohol for use in preparing cyclopropanecarboxylate and related insecticides, to insecticides employing this alcohol, and to an insecticidal method and composition. More particularly, the invention is directed to a 4-substituted-2-indanol intermediate for insecticidal esters, and to the insecticidal esters themselves. Of especial interest among the insecticidal esters of the invention is 4-phenyl-2-indanyl cis-3-(2-chloro-3,3,3-trifluoro-1-propenyl)-2,2-dimethylcyclopropanecarboxylate; particularly the enantiomer pair consisting essentially of a substantially equimolar mixture of S-4-phenyl-2-indanyl 1R,cis-3-(2-chloro-3,3,3-trifluoro-1-propenyl)-2,2-dimethylcyclopropanecarboxylate and R-4-phenyl-2-indanyl 1S,cis-3-(2-chloro-3,3,3-trifluoro-1-propenyl)-2,2-dimethylcyclopropanecarboxylate.

Pyrethrins, naturally occurring extracts of chrysanthemum flowers, have long been of interest as insecticides. Since elucidation of the structures of these compounds, synthesis efforts have been directed toward preparation of related compounds having enhanced insecticidal activity and improved stability toward air and light. Since a prerequisite for insecticidal activity of pyrethroids is the presence in one molecule of an appropriate acid moiety and an appropriate alcohol moiety, research in the art has been directed toward novel acid and/or alcohol radicals. Noteworthy advances in the area of alcohol research were the discovery of 5-benzyl-3-furylmethyl alcohol, then of the more photostable 3-phenoxybenzyl alcohol (see *Synthetic Pyrethroids*, ACS Symposium Series, No. 42, M. Elliott, Ed., American Chemical Society, Washington, D.C. 1977, Chapter 1). Similarly significant advances have been made in pyrethroid acid research. The commercial insecticide permethrin, the common name for 3-phenoxyphenylmethyl 3-(2,2-dichloroethenyl)-2,2-dimethylcyclopropanecarboxylate, exemplifies use of both newer acid and alcohol moieties in a single compound.

The present invention provides a novel indanyl alcohol and certain ester derivatives thereof which have a high level of insecticidal activity. It also provides a pyrethroid ester enantiomer pair and a process for producing it.

In this application, the term "lower" as applied to an aliphatic hydrocarbon group means having 1 to 6 carbon atoms, preferably 1 to 4 carbon atoms. The term "halo" or "halogen" means bromine, chlorine or fluorine. The term "haloalkyl" means an alkyl group of 1 to 3 carbon atoms substituted with 1 or more halogen atoms. The term "insecticide" is used in its broadest sense, and includes compounds possessing activity against true insects, acarids, and other household, veterinary or crop pests of the phylum Arthropoda. A "racemic modification" is a mixture of essentially equimolar parts of the optical isomers of a compound such that the mixture is essentially optically inactive. An "enantiomer pair" is a racemic modification consisting essentially of two enantiomers of a compound. These definitions are applicable throughout the specification and claims except where a contrary meaning is clearly indicated.

The novel compounds of this invention have the general formula

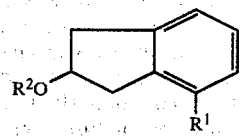

I in which $R^1$ is a phenyl, phenoxy, phenylthio, benzyl or heterocyclic radical which may be substituted with halogen, lower alkyl, halo(lower)alkyl, lower alkoxy, lower alkylthio, cyano or nitro; particularly halogen or lower alkyl. The heterocyclic radical is advantageously a 5 or 6 membered ring consisting of carbon and 1 to 3 ring members selected from oxygen, nitrogen, and sulfur. Suitable heterocyclic radicals include furanyl, thienyl, pyridyl, pyrimidyl, oxazolyl, isoxazolyl, thiazolyl, and isothiazolyl. Preferably, $R^1$ is phenyl which may be substituted with halogen or lower alkyl. More preferably, $R^1$ is unsubstituted phenyl.

$R^2$ is hydrogen; 2,2,3,3-tetramethylcyclopropylcarbonyl; 1-(substituted-phenyl)-2-methylpropyl-1-carbonyl, particularly 1-(4-chlorophenyl)-2-methylpropyl-1-carbonyl; or a group of the formula:

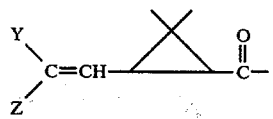

II wherein Y and Z, the same or different, are hydrogen, halogen, lower alkyl, perhalo(lower)alkyl, phenyl which may be substituted with halogen or lower alkyl, or phenylthio which may be substituted with halogen or lower alkyl, with the proviso that one of Y and Z is other than hydrogen. The novel alcohols are the compounds in which $R^2$ is hydrogen whereas in the insecticidal compounds $R^2$ is other than hydrogen.

Particularly useful insecticides or acaricides of the present invention are the cyclopropanecarboxylates in which one of Y and Z is halogen, such as chlorine or bromine, and the other, the same or different, is halogen or a perhaloalkyl group such as trihalomethyl, and $R^1$ is phenyl.

The cyclopropanecarboxylates having the acid residue of formula II have cis and trans isomeric forms, i.e., the carboxy and the substituted vinyl groups at the 1 and 3 positions of the cyclopropane ring are either cis or trans with respect to each other. Preparation of these compounds will usually yield a mixture of the cis and trans isomers, designated herein as cis,trans, in which the ratio of cis to trans may vary over a wide range. For purposes of this application the designations cis and trans are assigned in accordance with P. E. Burt, et al., *Pestic. Sci.*, 5 791–799 (1974). The compounds where Y is different from Z may also exist as E or Z isomers or as mixtures of E and Z isomers, designated E,Z, depending upon the spatial relationship of substituents on the α-carbon of the vinyl group to those on the β-carbon of the vinyl group.

In the cyclopropanecarboxylate art it is known there may be substantial differences in the level of insecticidal activity of the cis and trans isomers. In general, as between the cis and trans isomer of a given cyclopropanecarboxylate, the cis isomer is usually more active than the trans and also more active than the cis,-trans mixture. Similar differences in activity may also occur with respect to the E and Z isomers.

Unless a contrary intent is specifically expressed, this invention embodies and includes both cis and trans isomeric forms of the claimed compounds as well as mixtures thereof wherein the cis to trans ratio is within the range of 0:100 to 100:0. Similarly, the individual E and Z isomers, as well as the mixtures, are contemplated by and within the scope of the invention.

There may also be substantial differences in the level of insecticidal or acaricidal activity of the various optical isomers of any given pyrethroid ester of the present invention, and the different isomers and mixtures of them are also included within the scope of the invention. Thus, for example, for 4-phenyl-2-indanyl cis-3-(2-chloro-3,3,3-trifluoro-1-propenyl)2,2-dimethylcyclopropanecarboxylate, the present invention provides a racemic modification of the four possible optical isomers as well as an enantiomer pair of the 1R,cis/2'S and 1S,cis/2'R isomers. The absolute configuration of these isomers is shown in the structural formulas below. The designations 1R,cis and 1S,cis refer to the spatial relationship of the carbonyl group at the 1 position of the cyclopropane ring to the propenyl group at the 2 position of the ring, and the designations 2'R and 2'S refer to the absolute configuration at the C-2 carbon of the indanyl group.

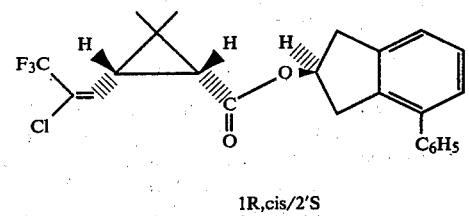

1R,cis/2'S

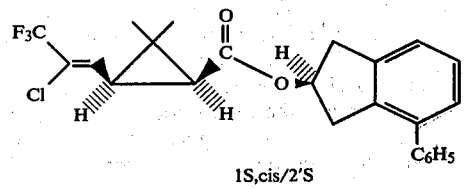

1S,cis/2'S

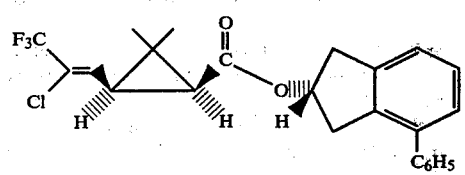

1S,cis/2'R

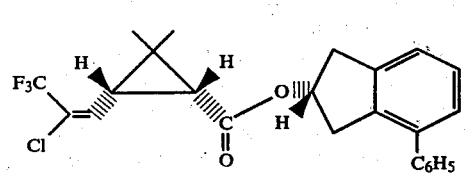

1R,cis/2'R

Preparation of this ester from racemic alcohol and racemic cis acid halide, such as is described in Example 8, results in the product being a mixture of all four possible optical isomers. This material is highly active insecticidally, and is shown in Example 10 to be generally superior in this respect to the commercial insecticide permethrin. The four isomer racemic modification can be resolved into two pairs of enantiomers, pairs A and B, by a chromatographic separation procedure such as preparative high pressure liquid chromatography on silica as exemplified in Example 9. Enantiomer pair A is a substantially equimolar mixture of the 1S,cis/2'S and 1R,cis/2'R isomers, and is inactive insecticidally under the conditions described in Example 10. Enantiomer pair B is a substantially equimolar mixture of the other two isomers, the 1R,cis/2'S and 1S,cis/2'R isomers. This enantiomer pair possesses outstanding insecticidal and acaricidal activity, and is generally far more active than the mixture of all four isomers.

The novel alcohols of this invention may be prepared in a number of ways. The schemata below for 4-phenyl-2-indanol is illustrative of methods by which the alcohols can be prepared. This method of preparation is described in greater detail in Example 1. Other methods include the hydroboration/oxidation and the epoxidation/reduction of an appropriate indene, such as compound H in the schemata below.

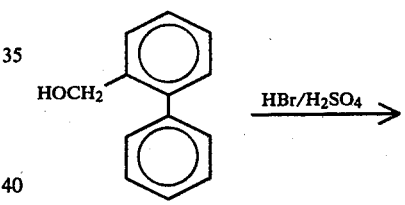

(A)

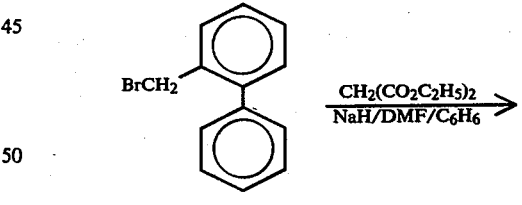

(B)

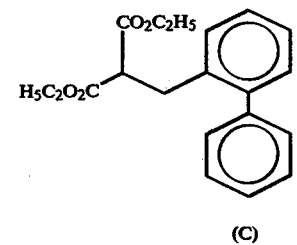

(C)

$$(C) \xrightarrow[2\ H_3O^\oplus]{1\ KOH/H_2O/C_2H_5OH}$$

-continued

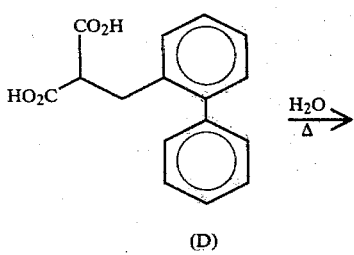

(D)

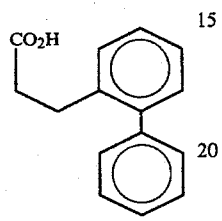

(E)

(E) $\xrightarrow[\text{2 ALCL}_3/\text{C}_6\text{H}_6]{\text{1 SOCL}_2}$

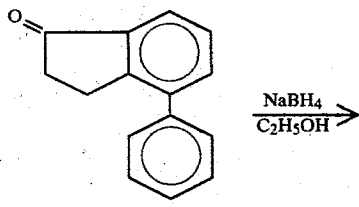

(F) $\xrightarrow[\text{C}_2\text{H}_5\text{OH}]{\text{NaBH}_4}$

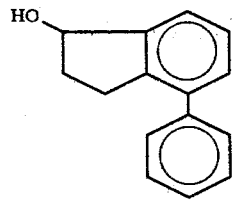

(G)

(G) $\xrightarrow[\text{C}_6\text{H}_6]{p\text{-CH}_3\text{C}_6\text{H}_4\text{SO}_3\text{H}}$

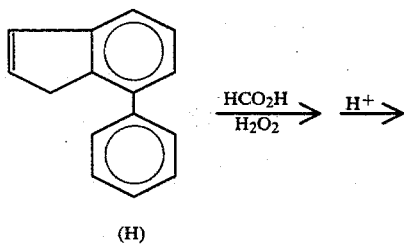

(H) $\xrightarrow[\text{H}_2\text{O}_2]{\text{HCO}_2\text{H}}$ $\xrightarrow{\text{H}^+}$ -continued (I)

(I) $\xrightarrow[\text{C}_2\text{H}_5\text{OH}]{\text{NaBH}_4}$

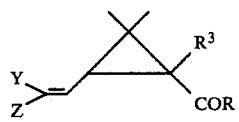

(J)

The insecticidal or acaricidal compounds having the acid residue of formula II may be prepared from alkanoates of the formula $$\begin{array}{c} X \quad Y \\ X \diagdown \diagup \\ \diagdown \diagup Z \\ \diagdown \text{COR} \\ R^3 \end{array} \qquad \text{III}$$

in which Y and Z are defined as above; R is lower alkoxy, such as methoxy or ethoxy, or a 4-substituted-2-indanyloxy moiety from an alcohol of formula I; $R^3$ is hydrogen, lower alkylcarbonyl, lower alkoxycarbonyl, or cyano, preferably hydrogen; and X is chloro or bromo. Example 2 illustrates a method for preparation of the alkanoate intermediates of Formula III whereby a lower alkyl 3,3-dimethyl-4-pentenoate is allowed to react with a compound of the formula $X_2C(Y)(Z)$ wherein X, Y, and Z are as defined above.

Dehydrohalogenation of the compound of formula III followed, if necessary, by hydrolysis of the ester and, also if necessary, halogenation of the resulting carboxyl group gives a compound of the formula $$\begin{array}{c} R^3 \\ Y \diagup \diagdown \diagup \\ Z \diagdown \text{COR} \end{array} \qquad \text{IV}$$

in which R is lower alkoxy, hydroxy, halogen, or a 4-substituted-2-indanyloxy moiety from an alcohol of formula I, and Y, Z and $R^3$ are as defined above. The dehydrohalogenation reaction may proceed through one or more intermediates of the formulas:

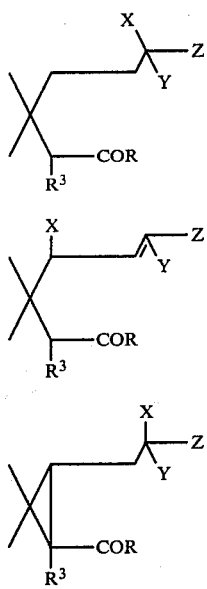

and may be conducted in a single step by elimination of 2 equivalents of hydrogen halide, HX, to give a compound of formula VI directly, or in multiple steps under conditions allowing a sequential elimination of the 2 equivalents of HX in separate reactions. These intermediates or mixtures thereof may be recovered if desired. The compound of formula IV is then converted to the compound of formula I by methods known to the art, for example, by removing $R^3$ (if other than hydrogen) and, where R is lower alkoxy, hydroxy, or halogen, esterifying or transesterifying with a 4-substituted-2-indanol of formula I ($R^2$ is hydrogen).

The examples which follow illustrate preparation of the insecticidal compounds and novel alcohol intermediates therefor in accordance with the general method described above. In the examples all temperatures are in degrees centigrade, all pressures are in mm Hg, and reduced pressure for concentrations of liquid was produced by a water aspirator unless otherwise specified.

Example 1 illustrates the preparation of compounds of formula I wherein $R^2$ is hydrogen.

EXAMPLE 1

SYNTHESIS OF 4-PHENYL-2-INDANOL

A. Preparation of 2-(bromomethyl)biphenyl

A stirred solution of 58.9 g (0.319 mole) of 2-biphenylmethanol and 6 ml of concentrated sulfuric acid in 67 ml of aqueous 48% hydrobromic acid was heated under reflux for 5 hours. The reaction mixture was cooled to ambient temperature, poured into ice-water, and the resulting mixture extracted with three portions of 100 ml each of diethyl ether. The combined extracts were washed with 50 ml of a saturated aqueous solution of sodium bicarbonate, then with 50 ml of water. The organic layer was dried with magnesium sulfate, filtered and the filtrate concentrated under reduced pressure to give 76.8 g of 2-(bromomethyl)biphenyl as a residual oil. The nmr and ir spectra were consistent with the proposed structure.

B. Preparation of diethyl (2-phenylbenzyl)malonate

A stirred mixture of 12.5 g (0.54 mole) of sodium hydride (25 g of a 50% dispersion in mineral oil) in 300 ml of dimethylformamide and 900 ml of benzene was placed under a nitrogen atmosphere and cooled to 0° C. To this mixture, 104.3 g (0.9 mole) of diethyl malonate was added dropwise during a 5 minute period and the mixture was stirred until hydrogen evolution ceased. 2-(Bromomethyl)biphenyl (117 g. 0.47 mole) was then added at 0° C. Upon complete addition the reaction mixture was stirred at 0° C. for 30 minutes, then was allowed to warm to ambient temperature with stirring for one hour. The reaction mixture was poured into 500 ml of water, the layers separated, and the aqueous layer washed with two portions of 250 ml each of diethyl ether. The organic layer was combined with the ether washings, and the whole was washed with one portion of 500 ml of aqueous 5% hydrochloric acid, one portion of 500 ml of water, one portion of 300 ml of a solution saturated with sodium bicarbonate, and finally, one portion of 500 ml of water. The organic layer was dried with magnesium sulfate, filtered, and the filtrate concentrated under reduced pressure to an oil residue. The oil was distilled under reduced pressure to give 149.0 g of diethyl (2-phenylbenzyl)malonate; b.p. 175°–180° C./0.8–0.9 mm. The nmr spectrum was consistent with the proposed structure.

C. Preparation of (2-phenylbenzyl)malonic acid

A stirred solution of 149.0 g (0.456 mole) of diethyl (2-phenylbenzyl)malonate and 56.1 g (1.0 mole) of potassium hydroxide in 50 ml of water and 500 ml of ethanol was heated under reflux for 3 hours. The reaction mixture was allowed to cool to ambient temperature and stand for 60 hours. The ethanol was removed by distillation and the residue slurried in 400 ml of water. The mixture was extracted with one portion of 250 ml of diethyl ether. The aqueous phase was separated and acidified with concentrated hydrochloric acid, then extracted with two portions of 250 ml each of diethyl ether. The two extracts of the acidified aqueous phase were combined, dried with magnesium sulfate, filtered, and the filtrate concentrated under reduced pressure to give (2-phenylbenzyl)malonic acid as a pale yellow oil. The oil was used directly in the next step of this reaction sequence.

D. Preparation of 3-(2-biphenyl)propionic acid

A solution of 124.2 g (0.46 mole) of the oil from step C of this Example in 500 ml of water was heated under reflux for 16 hours. The reaction mixture was cooled, and the product was collected by filtration to give, after recrystallization from ethanol-water, 92.9 g of 3-(2-biphenyl)propionic acid. The nmr spectrum was consistent with the proposed structure.

Analysis calc'd for $C_{15}H_{14}O_2$: C: 79.62, H: 6.24; Found: C: 79.84, H: 5.98.

E. Preparation of 4-phenyl-1-indanone

A solution of 92.9 g (0.41 mole) of 3-(2-biphenyl)propionic acid in 100 ml of thionyl chloride was stirred at ambient temperature for 16 hours. The excess thionyl chloride was removed by distillation followed by co-distillation with three 50 ml portions of benzene.

The residue was dissolved in 150 ml of benzene and was added dropwise at 10° C. over 15 minutes to a stirred mixture of 71.0 g (0.53 mole) of aluminum chloride in 900 ml of benzene. Upon complete addition the reaction mixture was stirred at 10° C. for 110 minutes then poured into 1000 ml of ice-water and stirred until the ice melted. The aqueous phase was separated and extracted with two portions of 100 ml each of diethyl ether. The ether extracts and the organic phase were combined and washed with a 10% aqueous solution of sodium hydroxide, then with two portions of water. The combined extracts were dried with magnesium sulfate, filtered, and the filtrate concentrated under reduced pressure to give, as a brown crystalline solid, 85.4 g of 4-phenyl-1-indanone, m.p. 85°–90° C. The product was used without further purification.

A sample was recrystallized for analytical purposes. The nmr spectrum was consistent with the proposed structure.

Analysis calc'd for $C_{15}H_{20}O$: C: 86.50, H: 5.81; Found: C: 86.63, H: 5.74.

F. Preparation of 4-phenyl-1-indanol

To a stirred solution of 20.8 g (0.10 mole) of 4-phenyl-1-indanone in 150 ml of ethanol was added portionwise 2.0 g (0.06 mole) of sodium borohydride. During the addition the reaction temperature rose to 33° C. Upon complete addition the reaction mixture was allowed to cool to ambient temperature and was stirred for 16 hours. The reaction mixture was mixed in water and concentrated under reduced pressure. A precipitate, which developed during concentration of the aqueous solution, was collected, dried, then recrystallized from toluene-hexane to give 17.3 g of 4-phenyl-1-indanol; m.p. 80.5°–81.5° C. The nmr spectrum was consistent with the proposed structure.

Analysis calc'd for $C_{15}H_{14}O$: C: 85.68, H: 6.71; Found: C: 85.63, H: 6.70.

G. Preparation of 7-phenyl-1H-indene

A stirred solution of 16.7 g (0.08 mole) of 4-phenyl-1-indanol and 0.1 g of p-toluenesulfonic acid in 180 ml of benzene was heated under reflux for one hour as by-product water was collected in a Dean-Stark trap. The reaction mixture was washed with two portions of 50 ml of a 5% aqueous solution of sodium bicarbonate, then with one portion of 50 ml of water. The organic phase was dried with magnesium sulfate, filtered, and the filtrate concentrated under reduced pressure, keeping the temperature under 50° C., to give 14.8 g of 7-phenyl-1H-indene. The nmr spectrum was consistent with the proposed structure.

Analysis calc'd for $C_{15}H_{12}$: C: 93.71, H: 6.29; Found: C: 93.47, H: 6.31.

H. Preparation of 4-phenyl-2-indanone

A stirred solution of 53.2 ml of formic acid and 10.5 ml of 30% hydrogen peroxide was heated to 35° C., and 14.5 g (0.075 mole) of 7-phenyl-1H-indene was added dropwise causing the reaction mixture temperature to rise to 41° C. Upon complete addition the reaction mixture was allowed to cool to ambient temperature and was stirred for 16 hours. The reaction mixture was concentrated under reduced pressure to give a residual semi-solid which was subjected to steam distillation in the presence of aqueous dilute sulfuric acid. The steam distillates were filtered to give 1.84 g of 4-phenyl-2-indanone; m.p. 133°–136° C. The nmr and the ir spectra were consistent with the proposed structure.

I. Preparation of 4-phenyl-2-indanol

To a stirred mixture of 0.30 g (0.0014 mole) of 4-phenyl-2-indanone in 10 ml of ethanol was added portionwise 0.03 g (0.0008 mole) of sodium borohydride. The resulting yellow colored solution was stirred at ambient temperature for 1.5 hours, then concentrated, and 50 ml of water was added. The mixture was extracted with two portions of 50 ml each of diethyl ether. The extracts were combined, dried with sodium sulfate, filtered and the filtrate concentrated under reduced pressure to give, after recrystallization from hexane, 0.13 g of 4-phenyl-2-indanol. The nmr and ir spectra were consistent with the proposed structure.

Example 2 illustrates the preparation of compounds of formula III.

EXAMPLE 2

Synthesis of Ethyl 3,3-dimethyl-4,6,6-trichloro-7,7,7-trifluoroheptanoate

A stirred solution of 44.6 g (0.267 mole) of ethyl 3,3-dimethyl-4-pentenoate, 100 g (0.533 mole) of 1,1,1-trichlorotrifluoroethane, 0.27 g (0.0027 mole) of cuprous chloride, and 8.2 g (0.134 mole) of ethanolamine in 270 ml of tertiary butyl alcohol, under a nitrogen atmosphere, was heated at reflux for 16 hours. The reaction mixture was cooled to ambient temperature and extracted with three portions of 100 ml each of diethyl ether. A precipitate formed in the extracts, and was removed by vacuum filtration. The filter cake was washed with two portions of 25 ml each of diethyl ether. The ether extracts were combined with the washings, and the whole was concentrated under reduced pressure to an oily residue. Remaining volatile components were removed from the residue under further reduced pressure using a vacuum pump. The residue was subjected to distillation under reduced pressure to give 78.3 g of ethyl 3,3-dimethyl-4,6,6-trichloro-7,7,7-trifluoroheptanoate; bp 85°–87° at 0.12–0.15 mm. The nmr spectrum was consistent with the assigned structure.

Examples 3 and 4 illustrate preparation of the lower alkyl esters of formula IV. Example 3 is a two-step process via the intermediate of formula VII. Example 4 is a one-step process.

EXAMPLE 3

Synthesis of Methyl Cis,trans-3-(2-chloro-3,3,3-trifluoro-1-propenyl)-2,2-dimethylcyclopropanecarboxylate

A. Preparation of methyl cis,trans-3-(2,2-dichloro-3,3,3-trifluoropropyl)-2,2-dimethylcyclopropanecarboxylate A stirred solution of 37.0 g (0.112 mole) of methyl 3,3-dimethyl-4,6,6-trichloro-7,7,7-trifluoroheptanoate, 50 ml of tert-butyl alcohol, 50 ml of dimethylformamide, and 50 ml of hexane, under an argon atmosphere, was cooled to −5° C. To the stirred solution was added dropwise a solution of 16.4 g (0.14 mole) of potassium tert-butoxide in 200 ml of tert-butyl alcohol at such a rate so as to maintain the reaction mixture temperature at −3° to −5° C. Upon complete addition, the reaction mixture was stirred for 4 hours at −3° to −5° C., then poured into a solution of 8.0 g of ammonium chloride in 250 ml of water. The mixture was extracted with two portions of 200 ml each of diethyl ether. The combined ether extracts were washed with two portions of 200 ml each of water. The ether layer was dried with sodium sulfate and filtered. The filtrate was evaporated under reduced pressure to a residual oil. The oil was distilled under reduced pressure to give 19.8 g of methyl cis,- trans-3-(2,2-dichloro-3,3,3-trifluoropropyl)-2,2-dimethylcyclopropanecarboxylate; b.p. 55°–57° C./0.09 mm Hg. The ir and the nmr spectra were consistent with the proposed structure.

Analysis calc'd for $C_{10}H_{13}Cl_2F_3O_2$: C: 40.98; H: 4.47; Found: C: 41.50; H: 4.41.

B. Synthesis of methyl cis,trans-3-(2-chloro-3,3,3-trifluoro-1-propenyl)-2,2-dimethylcyclopropanecarboxylate A stirred solution of 30.6 g (0.105 mole) of methyl cis,trans-3-(2,2-dichloro-3,3,3-trifluoropropyl)-2,2-dimethylcyclopropanecarboxylate and 17.6 g (0.116 mole) of 1,5-diazabicyclo[5.4.0]undec-5-ene in 100 ml of dimethylformamide was heated at 100° C. for 4 hours. The reaction mixture was cooled and poured into a solution of 37.2 ml of concentrated hydrochloric acid in 300 ml of water. The mixture was extracted with three portions of 200 ml each of diethyl ether. The combined ether extracts were washed with an aqueous saturated solution of sodium chloride. The ether layer was dried with sodium sulfate and filtered. The filtrate was evaporated under reduced pressure to give a residual oil. The oil was dissolved in hexane, treated with decolorizing carbon, and filtered. The filtrate was evaporated under reduced pressure to a residual oil. The oil was distilled under reduced pressure to give in three fractions 10.0 g of methyl cis,trans 3-(2-chloro-3,3,3-trifluoro-1-propenyl)-2,2-dimethylcyclopropanecarboxylate; b.p. 40°–60° C./0.05 mm. The ir and the nmr spectra were consistent with the proposed structure. The nmr spectra indicated an 88:12 mixture of cis: trans isomers.

Analysis calc'd for $C_{10}H_{12}ClF_3O_2$: C: 46.80; H: 4.71; Found: C: 46.91; H: 4.79.

EXAMPLE 4

Synthesis of ethyl cis,trans-3-(2-chloro-3,3,3-trifluoro-1-propenyl)-2,2-dimethylcyclopropanecarboxylate To a stirred solution of 78.3 g (0.228 mole) of ethyl 3,3-dimethyl-4,6,6-trichloro-7,7,7-trifluoroheptanoate in 200 ml of distilled ethanol was added dropwise at ambient temperature 500 ml of an ethanolic solution of sodium ethoxide prepared from 11.5 g of metallic sodium (0.50 mole). After complete addition, the reaction mixture was stirred for one hour at ambient temperature, then allowed to stand for 18 hours. The cloudy reaction mixture was filtered and the filtrate evaporated under reduced pressure to give a residue. The residue was slurried in 200 ml of water, and the mixture was extracted with three portions of 50 ml each of diethyl ether. The combined extracts were dried with sodium sulfate and filtered. The filtrate was evaporated under reduced pressure to give, as a residual oil, 58.5 g of ethyl cis,trans-3-(2-chloro-3,3,3-trifluoro-1-propenyl)-2,2-dimethylcyclopropanecarboxylate. The nmr and the ir spectra were consistent with the assigned structure and indicated the product was a mixture of approximately equal parts of cis and trans isomers.

Examples 5 and 6 illustrate preparation of the individual cis and trans isomers of the free acids of formula IV.

EXAMPLE 5

Synthesis of Trans and Cis,trans-3-(2-chloro-3,3,3-trifluoro-1-propenyl)-2,2-dimethylcyclopropanecarboxylic acid A solution of 16.2 g (0.06 mole) of ethyl cis, trans-3-(2-chloro-3,3,3-trifluoro-1-propenyl)-2,2-dimethylcyclopropanecarboxylate in 94 ml (0.078 mole) of a stock solution containing 3.34 g of sodium hydroxide, 94 ml of ethanol and 6 ml of water was stirred while heating under reflux for a period of 18 hours. The reaction mixture was concentrated under reduced pressure, 25 ml of water was added, and the mixture was acidified to pH1 using 6 N hydrochloric acid. The acidified mixture was extracted with two portions of 50 ml each of diethyl ether. The combined extracts were dried with magnesium sulfate and filtered. The filtrate was evaporated under reduced pressure to give a residue. The residue was heated with 50 ml of hexane. The hot hexane was decanted from a tarry residue and cooled to yield a solid precipitate, which was collected by filtration, then dried to give 3.3 g of solid, m.p. 97°–103° C. Concentration of the mother liquor provided a second fraction of solid weighing 0.8 g, m.p. 96°–103° C. Nmr spectra of the two fractions indicated the solids were each trans-3-(2-chloro-3,3,3-trifluoro-1-propenyl)-2,2-dimethylcyclopropanecarboxylic acid. The mother liquor was evaporated to a residue. The residue was taken up in 50 ml of hexane and the solution cooled in a freezer for 18 hours. A solid precipitate was collected by filtration and dried to give 4.3 g of a solid, m.p. 64°–74° C. An nmr spectrum indicated the solid was a 50/50 mixture of cis and trans isomers of 3-(2-chloro-3,3,3-trifluoro-1-propenyl)-2,2-dimethylcyclopropanecarboxylic acid.

EXAMPLE 6

Synthesis of cis and cis,trans-3-(2-chloro-3,3,3-trifluoro-1-propenyl)-2,2-dimethylcyclopropanecarboxylic acid A stirred solution of 90.0 g (0.35 mole) of methyl cis,trans-3-(2-chloro-3,3,3-trifluoro-1-propenyl)-2,2-dimethylcyclopropanecarboxylate (approximately 90% cis, prepared in accordance with Example 3B), 5.4 ml of concentrated sulfuric acid and 13.8 ml of water in 138 ml of acetic acid was heated under reflux for 1 hour. The reaction mixture was cooled and extracted with two portions of 100 ml each of diethyl ether. The combined extracts were dried with sodium sulfate, filtered, and the filtrate concentrated under reduced pressure to a solid residue. The residue was digested with 300 ml of hexane and the hexane solution was decanted from a dark, tarry residue and allowed to cool to ambient temperature. A solid precipitate formed and was collected by filtration to give 42.4 g of cis-3-(2-chloro-3,3,3-trifluoro-1-propenyl)-2,2-dimethylcyclopropanecarboxylic acid, as determined by NMR spectroscopy. A melting point was not determined. The melting point of another sample of cis acid prepared at a different time was 108°–110° C. The filtrate was concentrated and cooled to give 5.1 g of solid, identified by NMR spectroscopy to be a 50:50 mixture of cis,trans-3-(2-chloro-3,3,3-trifluoro-1-propenyl)-2,2-dimethylcyclopropanecarboxylic acid. The filtrate was cooled in dry ice to give an additional 8.1 g of a 50:50 mixture of the cis,trans isomers.

Example 7 illustrates preparation of the acid halides of formula IV.

EXAMPLE 7

Synthesis of cis-3-(2-chloro-3,3,3-trifluoro-1-propenyl)-2,2-dimethylcyclopropanecarbonyl chloride A stirred solution of 10.0 g (0.04 mole) of cis-3-(2-chloro-3,3,3-trifluoro-1-propenyl)-2,2-dimethylcyclopropanecarboxylic acid in 100 ml of toluene was heated to 80° C. To this solution at 80° C. was added dropwise over 10 minutes a solution of 10.5 g (0.08 mole) of oxalyl chloride in 5 ml of toluene, and the whole heated at 80° C. for 26 hours. The toluene and excess oxalyl chloride were removed by distillation to give a residual oil which was distilled under reduced pressure using a Kugelrohr distilling system to give 8.2 g of cis-3-(2-chloro-3,3,3-trifluoro-1-propenyl)-2,2-dimethylcyclopropanecarbonyl chloride; b.p. 85° C./0.09 mm. The nmr and ir spectra were consistent with the proposed structure.

Example 8 illustrates preparation of compounds of formula I wherein $R^2$ is other than hydrogen.

EXAMPLE 8

Synthesis of 4-phenyl-2-indanyl cis-3-(2-chloro-3,3,3-trifluoro-1-propenyl)-2,2-dimethylcyclopropanecarboxylate A stirred solution of 0.25 g (0.0012 mole) of 4-phenyl-2-indanol and 0.11 g (0.0014 mole) of pyridine in 10 ml of toluene was cooled to 5° C., and a solution of 0.28 g (0.0011 mole) of cis-3-(2-chloro-3,3,3-trifluoro-1-propenyl)-2,2-dimethylcyclopropanecarbonyl chloride, prepared in accordance with Example 7, in 5 ml of toluene was added portionwise. Upon complete addition the reaction mixture was stirred at ambient temperature for 2 hours. The reaction mixture was filtered and the filtrate concentrated under reduced pressure to a residual oil. The oil was placed on a silica gel pad, and the product was eluted with 50 ml of 1:1 hexane:toluene. The eluate was concentrated under reduced pressure at 100°–115° C./0.02 mm using a Kugelrohr distilling system to give 0.12 g of 4-phenyl-2-indanyl cis-3-(2-chloro-3,3,3-trifluoro-1-propenyl)-2,2-dimethylcyclopropanecarboxylate. The nmr spectrum was consistent with the proposed structure.

Analysis calc'd for $C_{24}H_{22}ClF_3O_2$: C: 66.28; H: 5.10; Found: C: 65.76; H: 5.28.

Example 9 illustrates resolution of a mixture of the four possible optical isomers of a compound of formula I wherein $R^2$ is a group of cis formula II into two enantiomer pairs.

EXAMPLE 9

Resolution of 4-phenyl-2-indanyl cis-3-(2-chloro-3,3,3-trifluoro-1-propenyl)-2,2-dimethylcyclopropanecarboxylate into enantiomer pairs Resolution of 4-phenyl-2-indanyl cis-3-(2-chloro-3,3,3-trifluoro-1-propenyl)-2,2-dimethylcyclopropanecarboxylate into enantiomer pairs was accomplished by liquid chromatography (LC) using a high pressure liquid chromatograph, Spectra-Physics Model 3500B, equipped with a 254 mu and 235 mu detector and a high purity microparticulate silica (10 um particle size) packed preparative column, 9.4 mm ID×50 cm long. The preparative column is commercially available in prepacked form under the Partisil Magnum 9 trademark from Whatman Inc., 9 Bridewell Place, Clifton, N.J., 07014.

A series of eight injections of 250 ul each of a solution of 250 mg of 4-phenyl-2-indanyl cis-3-(2-chloro-3,3,3-trifluoro-1-propenyl)-2,2-dimethylcyclopropanecarboxylate, which may be prepared by the method of Example 8, in 3 ml of 2,2,4-trimethylpentane was made under isocratic conditions, 5 ml/minute flow rate using n-heptane/methylene chloride/acetonitrile (95/4.75/0.25) as eluant. Three fractions were collected from each injection; initial, middle, and final fractions. A second series of eight injections of 250 ul of the above solution was made using hexane/methylene chloride/acetonitrile (95/4.75/0.25) as eluant. As before, initial, middle, and final fractions were collected from each injection.

The initial fractions, from both series of injections, were combined to give 0.059 g of enantiomer pair A, 95% pure by LC. Enantiomer pair A is an essentially equimolar mixture of S-4-phenyl-2-indanyl 1S,cis-3-(2-chloro-3,3,3-trifluoro-1-propenyl)-2,2-dimethylcyclopropanecarboxylate (1S,cis/2'S isomer) and its enantiomer R-4-phenyl-2-indanyl 1R,cis-3-(2-chloro-3,3,3-trifluoro-1-propenyl)-2,2-dimethylcyclopropanecarboxylate (1R, cis/2'R isomer).

The final fractions were combined to give 0.011 g of enantiomer pair B, 88% pure by LC. Enantiomer pair B is an essentially equimolar mixture of S-4-phenyl-2-indanyl 1R,cis-3-(2-chloro-3,3,3-trifluoro-1-propenyl)-2,2-dimethylcyclopropanecarboxylate (1R,cis/2'S isomer) and R-4-phenyl-2-indanyl 1S,cis-3-(2-chloro-3,3,3-trifluoro-1-propenyl)-2,2-dimethylcyclopropanecarboxylate (1S,cis/2'R isomer).

The middle fractions were combined to give 0.21 g of a mixture of enantiomer pairs A and B. The mixture was dissolved in 2.5 ml of 2,2,4-trimethylpentane, and rechromatographed, making seven injections of 250 ul each. The eluant was hexane/methylene chloride/acetonitrile (93/6.65/0.35). Initial, middle, and final fractions were collected from each injection. An additional 0.04 g of enantiomer pair A was obtained from the combined initial fractions. The combined final fractions gave an additional 0.051 g of enantiomer pair B, 96% pure by LC.

The 0.059 g sample of enantiomer pair A (95% pure) and the 0.051 g sample of enantiomer pair B (96% pure) were the samples for which the insecticidal data reported below were determined.

In the method aspect of this invention, an effective insecticidal or acaricidal amount of the compound of formula I wherein $R^2$ is other than hydrogen is applied to the locus where control is desired, i.e., to the insect or acarid itself or to the foliage or seeds of agricultural plants. The compounds are useful for the control of household, veterinary, and crop insects of the phylum Arthropoda and may be applied as technical material or as formulated product. Typical formulations include compositions of the active ingredient in combination with an agriculturally acceptable carrier or extender, preferably with a surface active agent, and optionally with other active ingredients. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of active ingredient depending upon the particular agent used, the additives and carriers used, other active ingredients, and the desired mode of application. With due consideration to these factors the active ingredient of a typical formulation may, for example, be suitably present at a concentration of about 0.01% up to about 99.5%, preferably 0.1% up to 90% or 95%, of the formulation. An agriculturally acceptable carrier may comprise about 99.5% by weight to as low as about 0.5% by weight of the formulation. Compatible surface active agents, if employed in a formulation, may be present at various concentrations, suitably in the range of 1 to 30% by weight of the formulation.

The formulation may be used as such or diluted to a desired use dilution with a diluent or carrier suitable for facilitating dispersion of the active ingredients. A concentration of the active ingredient in the use dilution may be in the range of 0.001% to about 50%, preferably up to about 10% by weight.

Many variations of spraying, dusting, and controlled or slow release compositions of a type known in the art may be used by substituting or adding an insecticidal compound or compounds of this invention into the compositions known or apparent to the art.

The insecticidal or acaricidal compounds of this invention may be formulated and applied with other compatible active agents including nematacides, insecticides, acaracides, fungicides, plant regulators, herbicides, fertilizers, and the like.

In applying these compounds, whether alone or with other agricultural chemicals, an effective insecticidal or acaricidal amount of the active ingredient must be applied. While the application rate will vary widely depending on the choice of compound, formulation, mode of application, plant species being protected, planting density and other like factors, a suitable use rate for agricultural crops may be in the range of 0.005 to 3 k/ha, preferably 0.01 to about 1 k/ha.

The insecticidal compounds of this invention were tested for insecticidal activity as described in Examples 10 and 11 below.

EXAMPLE 10

Topical Application Tests

Test A. Enantiomer pairs A and B of Example 9 were comparatively tested at a single high dosing rate by topical application against southern armyworm (*Spodoptera eridania* [Cramer]), Mexican bean beetle (*Epilachna varivestis* Mulsant), and large milkweed bug (*Oncopeltus fasciatus* [Dallas]). The insect species are identified in the table below as SAW, MBB, and MWB respectively.

Two replicates of ten test larvae per replicate were placed in 9 cm petri dishes, each lined with a piece of filter paper and a food source. To the second or third dorsal thoracic segment of each larvae was placed a one microliter droplet containing 5 mg of test compound/milliliter of acetone. A one microliter droplet of 5 mg/ml solution is equivalent to 5000 nanograms/insect. The tests were allowed to stand for 24 hours before observation for a toxic effect to be elicited by the test compound. An insect was considered dead if it could no longer right itself and move in an oriented pattern. The results of this test are shown in the following table.

| Compound of | Topical Application Test A | | |
|---|---|---|---|
| | % Kill at 5000 nanograms/insect | | |
| Example 9 | SAW | MBB | MWB |
| Enantiomer Pair A | 0 | 0 | 0 |
| Enantiomer Pair B | 100 | 100 | 100 |

This test exemplifies the wide disparity in insecticidal effectiveness of different optical isomers having the same gross chemical structure. Enantiomer pair A of Example 9, which is an equimolar mixture of the 1S,cis/2′S and 1R,cis/2′R isomers of 4-phenyl-2-indanyl cis-3-(2-chloro-3,3,3-trifluoro-1-propenyl)-2,2-dimethylcyclopropanecarboxylate, was completely inactive in this test, while enantiomer pair B, the corresponding 1R,cis/2′S and 1S,cis/2′R isomer mixture, gave 100% kill against all three insect species.

Test B. This test was conducted as described for Test A above except that multiple dosing rates and an additional insect species, cabbage looper (*Trichopulsia ni* [Hubner]), designated CL, were used. The compounds included in this test were the compound of Example 8, enantiomer pair B of Example 9 (EP-B), and, for comparison purposes, the commercial insecticide permethrin which is 3-phenoxyphenylmethyl cis,trans-3-(2,2-dichloroethenyl)-2,2-dimethylcyclopropanecarboxylate. The compound of Example 8 is an equimolar mixture of the four possible optical isomers of 4-phenyl-2-indanyl cis-3-(2-chloro-3,3,3-trifluoro-1-propenyl)-2,2-dimethylcyclopropanecarboxylate, while enantiomer pair B of Example 9 is an equimolar mixture of only two of those isomers, the 1R,cis/2′S and 1S,cis/2′R isomers. Relative potencies, based on a value of 1.0 for the compound of Example 8, were determined by computing and comparing appropriate $LD_{50}$ values. The results of this test are shown in the following table.

| | Topical Application Test B | | | |
|---|---|---|---|---|
| | Relative Potency | | | |
| Compound | SAW | MBB | MWB | CL |
| Permethrin | 1.82 | 0.30 | 0.63 | 0.67 |
| of Example 8 | 1.00 | 1.00 | 1.00 | 1.00 |
| of Example 9 (EP-B) | 0.98[a] | 1.71[b] | 3.06[c] | 2.18[d] |

[a] $LD_{50}$ = 41.93 nanograms/insect
[b] $LD_{50}$ = 3.31 nanograms/insect
[c] $LD_{50}$ = 137.3 nanograms/insect
[d] $LD_{50}$ = 52.16 nanograms/insect Overall, enantiomer pair B of Example 9 was the most active of the compounds tested. Against Mexican bean beetle, milkweed bug, and cabbage looper, it was from 1.7 to 3.1 times more active than the four isomer mixture of Example 8, and was from 3.3 to 5.7 times more active than permethrin. Permethrin was more active than the other test compounds against southern armyworm.

EXAMPLE 11

Foliar Application Test

The test compound was dissolved in 5–10 ml of acetone containing 0.25% octylphenoxypolyethoxyethanol. This solution was dispersed in a solution of 90% water, 9.75% acetone, and 0.25% octylphenoxypolyethoxyethanol to give a solution having 16 ppm (w/w)

active ingredient. Aliquots of this solution were diluted with an appropriate amount of water to provide solutions containing various concentrations of active ingredient. Test organisms and techniques were as follows: The activity against Mexican bean beetle (*Epilachna varivestis* Muls.) and southern armyworm (*Spodoptera eridania* [Cram.]) was evaluated by spraying the leaves of pinto bean plants with the test solution and infesting with 3rd instar larvae after the foliage had dried. The activity against the pea aphid (*Acyrthosiphon pisum* [Harris]) was evaluated on broad bean plants whose leaves were sprayed before infestation with adult aphids. The activity against two-spotted spider mite (*Tetranychus urticae* [Koch]) was evaluated on pinto bean plants the leaves of which were dipped or sprayed with test solution after infestation with adult mites. To prevent escape of the insects from the test site, the complete test plant or the incised leaves were placed in capped paper cups. The tests were transferred to a holding room at 80° C. and 50% relative humidity for an exposure period of at least 48 hours. At the end of this time the dead and living insects were counted and the percent kill was calculated. Results of these tests are summarized in the table below.

| Compound of Example 9 | Foliar Application Test | | | | |
|---|---|---|---|---|---|
| | Rate (ppm) | % Kill | | | |
| | | TSM | SAW | MBB | PA |
| Enantiomer Pair B | 8 | 95 | — | — | — |
| | 4 | 79 | — | — | — |
| | 2 | 41 | 90 | — | — |
| | 1 | 55 | 65 | — | 70 |
| | 0.5 | — | 10 | 95 | 55 |
| | 0.25 | — | 15 | 80 | 25 |

This test illustrates the effectiveness of enantiomer pair B against acarids and insects generally. The data shown for Mexican bean beetle indicate a particularly high susceptibility of members of the order Coleoptera to enantiomer pair B.

We claim:

1. An insecticidal enantiomer pair consisting essentially of a substantially equimolar mixture of S-4-phenyl-2-indanyl 1R,cis-3-(2-chloro-3,3,3-trifluoro-1-propenyl)-2,2-dimethylcyclopropanecarboxylate and R-4-phenyl-2-indanyl 1S,cis-3-(2-chloro-3,3,3-trifluoro-1-propenyl)-2,2-dimethylcyclopropanecarboxylate.

* * * * *